United States Patent [19]

Reisser

[11] Patent Number: 5,392,125
[45] Date of Patent: Feb. 21, 1995

[54] INSTRUMENT FOR DETERMINING VISUAL SURFACE PROPERTIES

[76] Inventor: Helmut Reisser, Rosenstrasse 6, D-8026 Ebenhausen, Germany

[21] Appl. No.: 981,327

[22] Filed: Nov. 24, 1992

[30] Foreign Application Priority Data

Nov. 25, 1991 [DE] Germany .................... 4138679

[51] Int. Cl.⁶ .................................... G01N 21/55
[52] U.S. Cl. .................................... 356/445; 356/446
[58] Field of Search ........... 356/446, 448, 445, 447; 250/227.29

[56] References Cited

U.S. PATENT DOCUMENTS

| | | | |
|---|---|---|---|
| 3,012,465 | 12/1961 | Goldberg | 356/136 |
| 3,999,864 | 12/1976 | Nutter | 356/212 |
| 4,285,597 | 8/1981 | Lamprecht et al. | 356/446 |
| 4,988,205 | 1/1991 | Snail | 356/446 |

FOREIGN PATENT DOCUMENTS

| | | |
|---|---|---|
| 0020971 | 1/1981 | European Pat. Off. |
| 0095759 | 12/1983 | European Pat. Off. |
| 356935 | 6/1980 | Germany |
| 1190564 | 5/1970 | United Kingdom |
| 1404573 | 9/1975 | United Kingdom |
| 2189881A | 11/1987 | United Kingdom |
| 2192454A | 1/1988 | United Kingdom |
| 2242977A | 10/1991 | United Kingdom |

OTHER PUBLICATIONS

Bruecker, "Measuring The Specular Reflection on Surfaces", *International Laboratories*, pp. 28–32, (1990).

Primary Examiner—Richard A. Rosenberger
Assistant Examiner—Robert Kim
Attorney, Agent, or Firm—Foley & Lardner

[57] ABSTRACT

An instrument for determining visual surface properties includes a generally cylindrical housing 10 with an illumination unit 12 and a photo cell 22 disposed in its upper portion. The beam A emitted by the illumination unit 12 passes through an optical system 19 disposed in a lower portion of the housing 10 and is directed by a first prism 20 at a predetermined angle onto the surface 11 under examination. The beam A' reflected at a predetermined angle by the surface 11 is deflected by a second prism 20', passes the same optical system 19 a second time and is received by the photo cell 22. A plurality of pairs of prisms with different angles of incidence and reflection are arranged concentrically about the central axis N of the housing 10. An inexpensive instrument is thus achieved which is small in the direction parallel to the surface under examination.

7 Claims, 2 Drawing Sheets

INSTRUMENT FOR DETERMINING VISUAL SURFACE PROPERTIES

BACKGROUND OF THE INVENTION

This invention relates to an instrument for determining visual surface properties, i.e. for physically objectivating surface properties as they are perceived by the human eye by physiologically and psychologically processing spectrally weighted reflected or scattered radiation, radiation subjected to interference, or fluorescence radiation, which originates from surfaces of objects. Examples of such surface properties are gloss, haze, fogging, colour, metal-effect, mother-of-pearl effect, etc. In order to follow the valuation functions of the eye, an instrument of this type must be capable quantitatively to detect the angular, phase and spectral distribution of the radiation remitted by the surface, based on a given geometry and spectral composition of the radiation incident on the surface. For all practical cases, one single measurement geometry will be insufficient to perform this task.

An instrument for determining visual properties of a surface, which comprising a source emitting a beam of radiation, a detector, and an optical system for directing the beam emitted by the radiation source onto the surface and the beam remitted from the surface onto the detector, is known from Austrian Patent Specification No. 356,935. In this instrument, the optical illumination and measurement system includes a lens and a bundle of optical fibres arranged along an axis that extends perpendicularly to the surface under examination the fibre bundle is split into a number of partial bundles for supplying the reflected light to a corresponding number of detectors. Different angles of illumination and reflection may be obtained only by tilting the instrument with respect to the surface.

"International Laboratory", September 1990, pages 28 to 32, discloses another instrument for determining visual surface properties, which comprises three measuring arrangements in which the angles of incidence and reflection, related to the normal of the surface under examination, are 20°/20°, 60°/60°, and 85°/85°. Each of these three measuring arrangements includes a radiation source, a first optical system which directs the beam emitted by the radiation source onto the surface, a detector, and a second optical system which directs the beam remitted by the surface onto the detector. The large number of optical components required renders the known instrument complicated and expensive. Moreover, the known instrument has a considerably long basic surface to be placed on the surface under examination, so that it permits measurements only on correspondingly large, or freely accessible, plane surfaces.

Other prior-art instruments use one single measurement geometry only and are accordingly less complicated and smaller. For a complete valuation of the visual surface properties, however, a plurality of such instruments with different geometries are required, which results in even higher overall expenses.

SUMMARY OF THE INVENTION

It is an object of the invention to provide an instrument for determining visual surface properties which permits measurements even on small and accordingly difficult to access surface areas at minimum expense.

To meet this object, the instrument for determining visual properties of a surface in accordance with the present invention comprises a source emitting a beam of radiation, a detector, an optical system, and a pair of beam deflecting elements disposed between the optical system and the surface, of which one beam deflecting element directs the beam emitted by the radiation source at a predetermined angle onto the surface, and the other beam deflecting element directs the beam remitted from the surface at a predetermined angle onto the detector.

The instrument according to the invention uses the same one optical system (which in the simplest case may be just one lens) to direct both the beam emitted by the radiation source onto the surface under examination and the beam remitted by the surface onto the detector. This is accomplished by the fact that both beams pass through deflecting components provided between the optical system and the surface. Since the instrument requires but one single optical system, the latter may be highly corrected without rendering the overall expense of the instrument uneconomic.

The fact that the measuring beam passes the same optical system twice results in an automatic correction of the most important image errors, such as astigmatism. The beam deflecting components that are used further allow the instrument to have small dimensions in the direction parallel to the surface under examination and yet a comparatively large focal length, irrespective of the entrance and exit angles. The use of optical components of large focal lengths is advantageous as greater manufacturing tolerances are permissible.

Preferably, the beam emitted by the radiation source and the beam incident on the detector travel essentially perpendicularly to the surface under examination. This results in a particularly handy and slim instrument for taking measurements even on small surface regions that are difficult to access.

In another preferred embodiment, at least one further pair of beam deflecting elements, which have angles of incidence and remission with respect to the surface under examination different from the first pair, are disposed between the optical system and the surface, and the plane of the first beam path is rotated with respect to the plane of the further beam path about a central axis perpendicular to the surface. A concentric arrangement of a plurality of measuring units is thus achieved which use the same one optical system.

In the further embodiment, one single radiation source and one single detector are provided which are adapted to be aligned with each pair of beam deflecting elements by being rotated in common about the central axis. A single radiation source and detector may thus be utilised for the different measuring geometries.

A particularly easy to handle device is obtained by including the optical system and the beam deflecting elements in a generally cylindrical first housing portion and the radiation source and the detector in a generally cylindrical second housing portion which is rotatable about the central axis with respect to the first housing portion.

In accordance with another preferred embodiment, the beam emitted by the radiation source and the beam remitted from the surface cross each other. This is advantageous in that the various beams pass through the central area of the optical system where image errors are smallest.

Polarisation effects are avoided by using totally reflecting prisms in accordance with yet another embodiment of the invention.

DETAILED DESCRIPTION OF PREFERRED EMBODIMENTS

Figure 2:
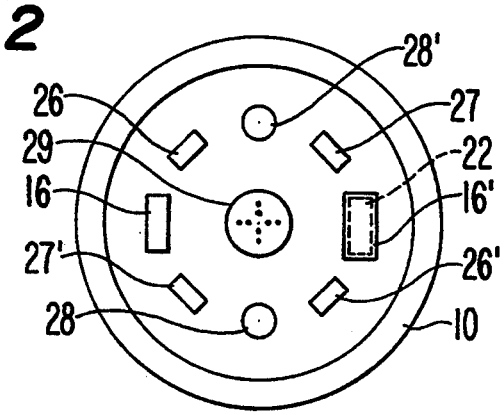
FIG. 2 is a cross-section along the line II—II of FIG. 1.
Figure 1:
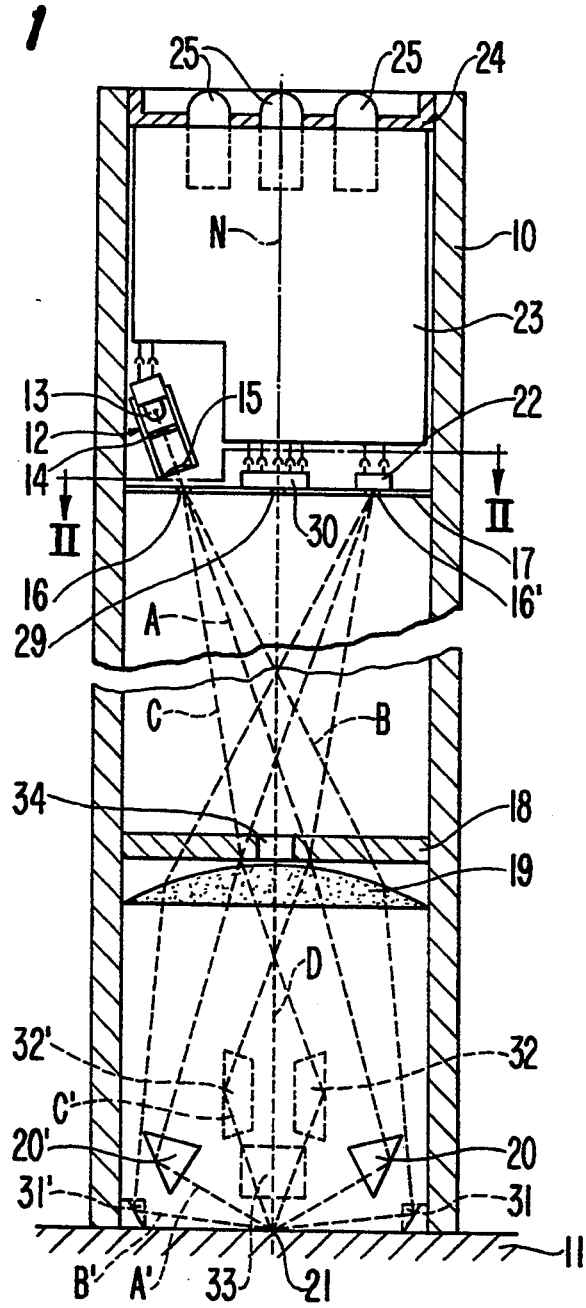
FIG. 1 is a longitudinal section through an instrument according to a first embodiment of the invention.

The instrument shown in FIGS. 1 and 2 has a cylindrical tubular housing 10 adapted to be placed upright with its lower surface on the surface 11 under examination. An illumination unit 12 is disposed within the upper housing portion and includes a light source 13, a diaphragm 14 forming the measuring spot, and an auxiliary optical system 15.

The light beam A which is emitted by the illumination unit 12 and is shown in FIG. 1 by a heavy dashed line, first passes through an aperture 16 which is provided in a diaphragm disc 17 extending perpendicularly to the axis N of the housing 10. The light beam A further passes through a filter disc 18 disposed further below in the housing 10 and extending perpendicularly to the axis N, and through an optical system 19 disposed therebelow, which optical system is represented in FIG. 1 as a single convex lens, and is deflected by a totally reflecting prism 20 in such a way that it is incident on the measuring spot 21 of the surface 11 at an angle of 60° with respect to the axis N, i.e. with respect to the normal of the surface 11.

The beam A', which is reflected (or generally remitted) by the measuring spot 21 at an angle of 60° with respect to the axis N, is deflected by a further totally reflecting prism 20', passes again through the optical system 19 and the filter disc 18 and penetrates a further aperture 16' in the diaphragm disc 17 to reach a photo cell 22. The signal received by the photo cell 22 is evaluated by an electronic unit 23 disposed within the upper portion of the housing 10.

A power supply (not shown) is also situated within the upper housing portion besides the electronic unit 23. A cover 24, which closes the top of the housing, carries operating and reading components schematically represented at 25 in FIG. 1.

As shown in FIG. 2, the diaphragm disc 17 has a total of eight apertures 16, 16', 26, 26', 27, 27', 28 and 28', mutually spaced 45° in the circumferential direction and disposed in pairs diametrically opposite each other, and a central aperture 29.

Above the apertures 26, 27, 28 and 28', further illumination units (not shown) are provided which essentially correspond to the illumination unit 12 of FIG. 1. Above the apertures 26', 27' and 29, further photo cells (not shown) are disposed which correspond to the photo cell 30 provided above the central aperture 29 in FIG. 1.

In the representation of FIG. 1, three further beams identified by B, B', C, C' and D are shown in addition to the beam A, A'. It should be understood that the beam B which is shown by a faint dashed line originates from the illumination unit (not shown) disposed above the aperture 26, passes the filter disc 18 and the optical system 19, and is directed by a prism 31 onto the measuring spot 21 at an angle of 85° with respect to the axis N. The beam B', which is reflected from the measuring spot 21 at an angle of 85°, is deflected by a further prism 31', passes again through the optical system 19 and the filter disc 18 and reaches the photo cell (not shown) disposed above the aperture 26'.

In a similar manner, the light beam C which is also shown by a faint dashed line in FIG. 1 and is emitted by the illumination unit (not shown) disposed above the aperture 27, travels through the filter disc 18 and the optical system 19 to a further prism 32 and is directed by the latter onto the measuring spot 21 at an angle of 20° relative to the axis N, and the beam C' reflected from the measuring spot 21 at the same angle is deflected by a further prism 32' and passes through the optical system 19 and the filter disc 18 to reach a further photo cell (not shown) disposed above the aperture 27'.

The measuring geometries using the beams A, B and C serve for standard gloss measurements, with the 20°/20° measuring geometry specifically for detecting high-gloss and the 85°/85° measuring geometry specifically for detecting mattgloss. The same instrument—with correspondingly modified measuring geometries—may be used for detecting other surface properties such as haze, fogging, metal effect, mother-of-pearl effect, etc.

As can be seen from the above description and FIG. 1, the beams which are emitted by the illumination unit 12 and are incident on the photo cell 22, due to their deflection in the prisms travel along substantially steeper paths than the beams incident on and reflected by the surface 11, and may therefore be considered to be essentially coaxial with the axis N. This results in the overall slim structure of the instrument.

As explained with reference to FIG. 2, the pairs of apertures 16—16', 26—26' and 27—27' are disposed in a plane containing the axis N, but at different angles with respect thereto. The pairs of prism 20—20', 31—31', and 32—32' are disposed in correspondingly different radial planes. As a result, the three illuminating arrangements thus formed are concentrically distributed about the axis N. (It is only for the sake of simplifying FIG. 1, that the three beams A, B and C are shown in the same plane.)

Each of the two illumination units disposed above the apertures 28 and 28' generates a light beam identified by D in FIG. 1, which is directed by a prism 33 onto the measuring spot 21 at an angle of 45°. This case uses the beam which is reflected along the axis N, passes through the optical system 19, an opening 34 centrally provided in the filter disc 18, and the central aperture 29, and is detected by the photo cell 30. This 45°/0° measuring arrangement, which uses the beam D, serves for measuring colour.

In an alternative embodiment, a detector may be disposed above the aperture 28' and may be used together with the illumination unit disposed above the aperture 28 to achieve a 45°/45° measuring geometry.

Instead of the above embodiment having a plurality of circumferentially arranged illumination units 12 and diametrically opposite photo cells 22, it is possible to make the upper housing portion, which contains these components, rotatable about the axis N with respect to the lower housing portion, which contains the diaphragm disc 17, the filter disc 18, the optical system 19 and the prisms 20, 20', 31, 31', 32, 32' and 33. In this case, the single illumination unit 12 may be directed to the corresponding aperture by a relative rotation between the two housing portions and may thus be utilised for the respective measuring geometry, wherein the single photo cell 22 is simultaneously aligned with the diametrically opposite aperture. By rotating the housing portions, the measuring signals, that result from illuminating the surface 11 at different angles, are obtained one after the other and are together processed by the electronic unit 23.

Figure 3:
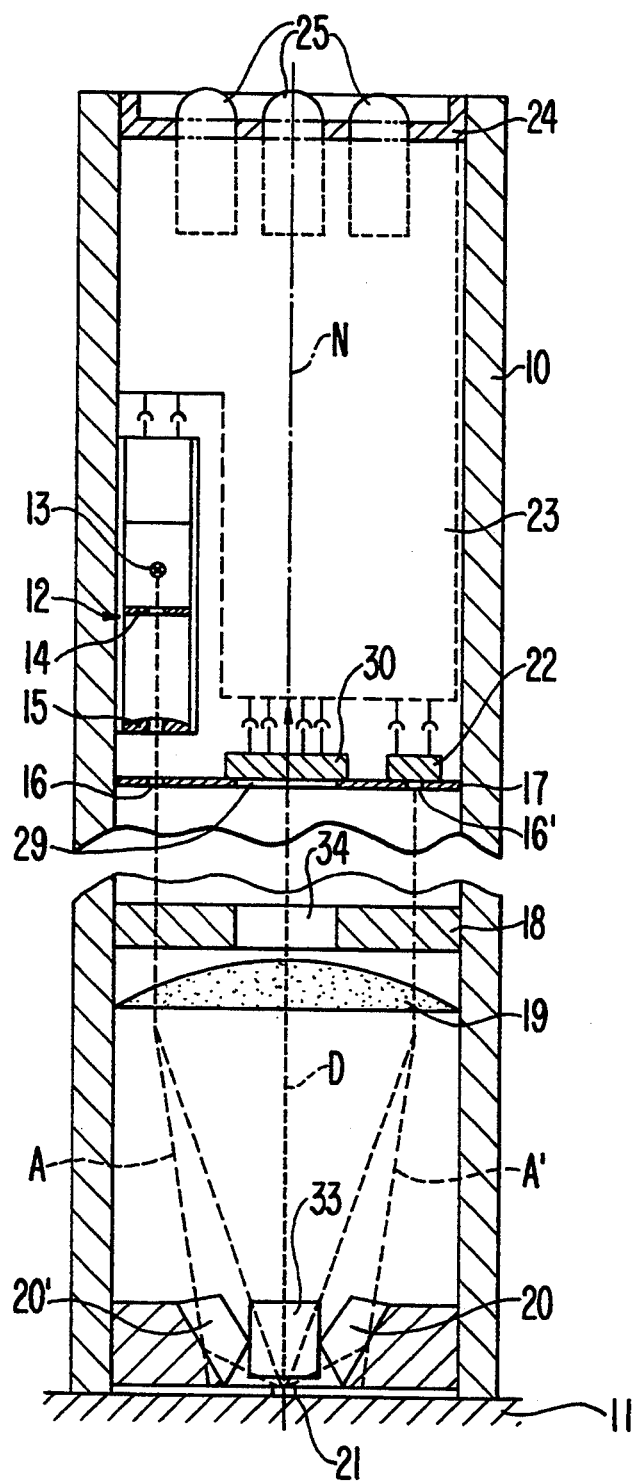
FIG. 3 is a longitudinal section through an instrument according to a second embodiment.

The alternative embodiment of the instrument according to FIG. 3 differs from the one of FIG. 1 in that the illumination unit 12 is so arranged that the beam emitted thereby, and similarly the remitted beam incident on the photo cell 22, travel parallel to the axis N. As a result, and in contrast to the embodiment of FIG. 1, the beams A and A', B and B', C and C' do not cross each other. In this case, all beams pass through the peripheral portion of the optical system 19 where any lens errors are more pronounced. On the other hand, lens errors are automatically compensated due to the fact that the optical system 19 is penetrated twice, provided the optical system is symmetrical.

In a further alternative, the prisms 32, 32' may be omitted and the 20°/20° beam may be made emerging from the illumination unit 20 and incident on the photo cell 22 at this angle directly.

In the above examples, it has been assumed that totally reflecting prisms are used for deflecting the beams A, B, C and D. Instead of this, it is principally possible to use mirrors which permit an even more compact structure, although they are disadvantageous for their polarisation effects.

I claim:

1. An instrument for determining visual properties of a surface, comprising
   a source emitting a beam of radiation,
   a detector,
   a lens objective, and
   a first pair of totally reflecting elements disposed between said lens objective and said surface, of which one of said first pair of totally reflecting elements directs the beam emitted by said radiation source at a predetermined angle onto said surface, and the other of said first pair of totally reflecting elements directs the beam remitted from said surface at a predetermined angle onto said detector, and wherein the beam emitted by said radiation source and the beam remitted from said surface transmit the same lens objective.

2. The instrument of claim 1, wherein the path of the beam emitted by said radiation source and the path of the beam incident on said detector are substantially perpendicular to said surface over an essential portion of their lengths.

3. The instrument of claim 1, further including at least a second pair of totally reflecting elements which have angles of incidence and remission with respect to said surface different from the first pair of totally reflecting elements and are disposed between said lens objective and said surface, and wherein a plane of a first beam path created by said first pair of totally reflecting elements is rotated with respect to a plane of a second beam path created by said second pair of totally reflecting elements about a central axis perpendicular to said surface.

4. The instrument of claim 3, wherein one single radiation source and one single detector are provided which are adapted to be aligned with each pair of said first and second pairs of totally reflecting elements by being rotated in common about said central axis.

5. The instrument of claim 4, further including a generally cylindrical first housing portion which contains said lens objective and said first and second pairs of totally reflecting elements, and a generally cylindrical second housing portion which contains said radiation source and said detector and which is rotatable about said central axis with respect to said first housing portion.

6. The instrument of claim 1, wherein the beam emitted by said radiation source and the beam remitted from said surface cross each other.

7. The instrument of claim 1, wherein said first and second pairs of totally reflecting elements consist of prism.

* * * * *